US011413298B2

(12) United States Patent
Stöckl et al.

(10) Patent No.: US 11,413,298 B2
(45) Date of Patent: Aug. 16, 2022

(54) MEDICAMENT FOR PREVENTION OF TREATMENT OF RHINOVIRUS INFECTION

(71) Applicant: MEDIZINISCHE UNIVERSITAT WIEN, Vienne (AT)

(72) Inventors: Johannes Stöckl, Vienna (AT); Guido Gualdoni, Vienna (AT)

(73) Assignee: MEDIZINISCHE UNIVERSITAT WIEN, Vienna (AT)

( * ) Notice: Subject to any disclaimer, the term of this patent is extended or adjusted under 35 U.S.C. 154(b) by 0 days.

(21) Appl. No.: 16/770,482

(22) PCT Filed: Dec. 28, 2018

(86) PCT No.: PCT/EP2018/097060
§ 371 (c)(1),
(2) Date: Jun. 5, 2020

(87) PCT Pub. No.: WO2019/149436
PCT Pub. Date: Aug. 8, 2019

(65) Prior Publication Data
US 2020/0397805 A1   Dec. 24, 2020

(30) Foreign Application Priority Data
Jan. 30, 2018  (EP) .................................... 18154088

(51) Int. Cl.
*A61K 31/7004* (2006.01)
*A61P 31/16* (2006.01)
*A61K 9/00* (2006.01)
*A61K 45/06* (2006.01)

(52) U.S. Cl.
CPC .......... *A61K 31/7004* (2013.01); *A61K 9/008* (2013.01); *A61K 9/0043* (2013.01); *A61K 9/0075* (2013.01); *A61K 9/0078* (2013.01); *A61K 45/06* (2013.01); *A61P 31/16* (2018.01)

(58) Field of Classification Search
CPC .... A61K 31/7004; A61K 45/06; A61K 9/008; A61K 9/0078; A61K 9/0075; A61K 9/0043; A61P 31/16
See application file for complete search history.

(56) References Cited

U.S. PATENT DOCUMENTS

| 4,603,122 | A | 7/1986 | Blough | |
| 2012/0065150 | A1* | 3/2012 | Hutchinson | A61P 25/00 514/23 |

FOREIGN PATENT DOCUMENTS

| DE | 197 06 489 A1 | 9/1998 |
| DE | 19706489 A1 | 9/1998 |
| WO | WO 2013/077881 | 5/2013 |
| WO | WO 2012/077828 | 5/2014 |

OTHER PUBLICATIONS

Knowles et al., Journal of Virology, May 1976, 18(2), p. 644-651. (Year: 1976).*
Kourbeti et al., Clin. Microbiol. Infect., 2012, 18, p. 359-364. (Year: 2012).*
Examination Report from the European Patent Office issued in corresponding Application No. 18 833 069.0, dated May 25, 2021.
Ojima et al., "Preparation of a fine powder of 2-deoxy-2-[18F]fluoro-D-glucose suitable for inhalation to diagnose lung diseases by means of PET", *Ann Nucl Med.*, 3(3):143-147, 1989.
Venegas et al., "Lung physiology and aerosol deposition imaged with positron emission tomography", *J Aerosol Med Pulm Drug Deliv.*, 26(1):1-8, 2013.
Kang et al., "2-Deoxyglucose: an anticancer and antiviral therapeutic, but not any more a low glucose mimetic", *Life Sci.*, 78(12):1392-1399, 2006.
Schnitzer et al., "Effect of 2-deoxy-D-glucose and glucosamine on the growth and functions or respiratory syncytial and parainfluenza 3 viruses", *Virology.*, 67(1):306-309, 1975.
Kilbourne; E.D., "Inhibition of influenze virus multiplication with a glucose antimetabolite (2-deoxy-D-glucose)", *Nature.*, 183(4656):271-272, 1959.
Arita et al., "Studies on antiviral glycosides. Synthesis and biological evaluation of various phenyl glycosides", *Carbohydr Res.*, 62(1):143-154, 1978.
Hodes et al., "Inhibition of Respiratory syncytial, parainfluenza 3 and measles viruses by 2-deoxy-D-glucose", *Virology.*, 63(1):201-208, 1975.
Courtney et al., "Effects of 2-deoxcy-D-glucose on herpes simplex virus replication", *Virology.*, 52(2):447-455, 1973.
Bartlett et al., "Mouse models of rhinovirus-induced disease and exacerbation of allergic airway inflammation", *Nature Medicine*, 14(2):199-204, 2008.
Bertino; Joseph S., "Cost of Burden of Viral Respiratory Infections: Issues for Formulary Decision Makers", *Am J Med.*, 112 Suppl 6A:42S-49S, 2002.
Blaas and Fuchs, "Mechanism of human rhinovirus infections", *Molecular and Cellular Pediatrics*, 3(1):21, 2016.
Fleisher and Laessig, "Safety and efficacy of pleconaril for treatment of the common cold", *Clin Infect Dis.*, 37(12):1722, 2003.
Gschwandtner et al., "Proteome analysis identifies L1CAM/CD171 and DPP4/CD26 as novel markers of human skin mast cells", *Allergy*, 72(1):85-97, 2017.

(Continued)

*Primary Examiner* — Jonathan S Lau
(74) *Attorney, Agent, or Firm* — Norton Rose Fulbright US LLP (57) ABSTRACT

The present invention provides a pharmaceutical composition for use in prevention or treatment of a human rhinovirus (HRV) infection. The composition comprises an aldohexose, wherein the hydroxyl group at carbon 2 of the aldohexose is replaced by any one of H, F, Cl, Br, I, SH, Me, OMe and SMe, such as a 2-deoxy-glucose. Furthermore, a dispenser for intranasal administration, such as a nasal spray or nose drop applicator containing said pharmaceutical composition is provided. In addition, an inhalation device, such as a metered-dose inhaler, a dry-powder inhaler or a nebuliser, comprising said composition is provided.

12 Claims, 4 Drawing Sheets

(56) References Cited

OTHER PUBLICATIONS

Gualdoni et al., "Azithromycin inhibits IL-1 secretion and non-canonical inflammasome activation", *Sci Rep*, 5:12016, 2015.
Kaiser et al, "Chronic Rhinoviral Infection in Lung Transplant Recipients", *Am J Respir Crit Care Med.*, 174(12):1392-1399, 2006.
Liu et al., "Long-term impact of respiratory viral infection after pediatric lung transplantation", *Pediatr Transplant*, 14(3):431-436, 2010.
Palmenberg et al., "Sequencing and Analyses of All Known Human Rhinovirus Genomes Reveal Structure and Evolution", 324(5923):55-59, 2009.
Papi et al., "Infections and airway inflammation in chronic obstructive pulmonary disease severe exacerbations", *Am J Respir Crit Care Med.*, 173(10): 1114-1121, 2006.
Steinke and Borish, "Immune Responses in Rhinovirus-Induced Asthma Exacerbations" *Curr Allergy Asthma Rep*, 16(11 ):78, 2016.
Sun and Whittaker, "Entry of influenza virus", *Adv Exp Med Biol.*, 790:72-882, 2013.
Watanabe and Kawaoka, "Influenza virus-host interactomes as a basis for antiviral drug development", *Curr Opin Virol.*, 14:71-78, 2015.
Arita et al., "Studies on antiviral glycosides. Synthesis and biological evaluation of various phenyl glycosides", *Carbohydrate Research*, vol. 62, No. 1, Apr. 1, 1978, pp. 143-154.
Bartlett et al., "Mouse models of rhino virus-induced disease and exacerbation of allergic airway inflammation", *Nature Medicine*, 14:199-204 (2008).
Bertino, J.S., "Cost of Burden of Viral Respiratory Infections: Issues for Formulary Decision Makers", *Am J Med.*, 112(6A):42S-49S (2002).
Blaas et al., "Mechanism of human rhino virus infections", *Molecular and Cellular Pediatrics*, 3:21 (2016).
Courtney et al., "Effects of 2-deoxy-d-glucose on herpes simplex virus replication", *Virology*, vol. 52, No. 2, Apr. 1, 1973, pp. 447-455.
Extended European Search Report issued in corresponding Application No. EP 18 15 4088 dated Jul. 16, 2018.
Fleishcer et al, "Safety and Efficacy Evaluation of Pleconaril for Treatment of the Common Cold", *Clin Infect Dis.*, 37(12):1722 (2003).
Gschwandtner, M., "Proteome analysis identifies L1CAM/CD171 and DPP4/CD26 as novel markers of human skin mast cells", *Allergy*, 72:85-97 (2017).
Gualdoni, G., "Azithromycin inhibits IL-1 secretion and non-canonical inflammasome activation", *SciRep*, 5:12016 (2015).
Hodes et al., "Inhibition of respiratory syncytial, parainfluenza 3 and measles viruses by 2-deoxy-d-glucose". *Virology*, vol. 63, No. 1, Jan. 1, 1975, pp. 201-208.
International Search Report issued in corresponding International Patent Application No. PCT/EP2018/097060 dated Jun. 14, 2019.
Kaiser et al., "Chronic Rhinoviral Infection in Lung Transplant Recipients", *Am J Respir Crit Care Med*, 174:1392-1399 (2006).
Kang et al., "2-Deoxyglucose: An anticancer and antiviral therapeutics, but not any more a low glucose mimetic", *Life Sciences*, vol. 78, No. 12, Feb. 16, 2006, pp. 1392-1399.
Kilbourne, E.D., "Inhibition of Influenza Virus Multiplication with a Glucose Antimetabolite (2-deoxy-D-glucose)", *Nature*, vol. 183, Jan. 1, 1959, pp. 271-272.
Liu et al., "Long-term impact of respiratory viral infection after pediatric lung transplantation", *Pediatr Transplantation*, 14:431-436 (2010).
Ojima, Fumiyoshi et al., "Preparation of a fine powder of 2-deoxy-2-[18F]fluoro-D-glucose suitable for inhalation to diagnose lung diseases by means of PET", *Annals of nuclear medicine*, Nov. 1, 1989, pp. 143-147.
Palmenberg et al., "Sequencing and Analysis of All Known Human Rhino virus Genomes Reveal Structure and Evolution", *Science*, 324:55-59 (2009).
Papi et al., "Infections and Airway Inflammation in Chronic Obstructive Pulmonary Disease Severe Exacerbations", *Am J Respir Crit Care Med*, 173:1114-1121 (2006).
Schnitzer et al., "Effect of 2-deoxy-D-glucose and glucosamine on the growth and functions of respiratory syncytial and parainfluenza 3 viruses", *Virology*, vol. 67, No. 1, Sep. 1, 1975, pp. 306-309.
Steinke et al., "Immune Responses in Rhino virus-Induced Asthma Exacerbations", *Curr Allergy Asthma Rep*, 16:78 (2016).
Sun et al., "Entry of Influenza Virus", *Viral Entry into Host Cells*, chapter 4, pp. 72-73 (2006).
Venegas et al., "Lung Physiology and Aerosol Deposition Imaged with Positron Emission Tomography", *Journal of Aerosol Medicine and Pulmonary Drug Delivery*, vol. 26, No. 1, Feb. 1, 2013, pp. 1-8.
Watanabe et al., "Influenza Virus-Host Interactomes as a Basis for Antiviral Drug Development", *Curr Opin Virol.*, 14:71-78 (2015).
Written Opinion of the ISR issued in corresponding International Patent Application No. PCT/EP2018/097060 dated Jun. 14, 2019.

* cited by examiner

Placebo

MEDICAMENT FOR PREVENTION OF TREATMENT OF RHINOVIRUS INFECTION

CROSS-REFERENCE TO RELATED APPLICATIONS

This application is a national phase application under 35 U.S.C. § 371 of International Application No. PCT/EP2018/097060 filed Dec. 28, 2018, which claims priority to EP Application No. 18154088.1 filed Jan. 30, 2018; the entire contents of each of the referenced disclosures is specifically incorporated by reference herein without disclaimer.

The present invention relates to pharmaceutical compositions for use in prevention or treatment of a human rhinovirus (HRV) infection, such as the common cold.

HRV is an ssRNA non-enveloped virus of the family of the Picornaviridae. It causes the common cold, a condition responsible for several billion dollars of healthcare costs (Bertino, 2002), and is the causative agent of lower respiratory tract infection in the immunosuppressed (Kaiser et al., 2006; Liu et al., 2010) and both chronic obstructive pulmonary disease (COPD) and asthma exacerbations (Papi et al., 2006; Steinke and Borish, 2016).

To date, therapeutic treatment options effective against HRV are very limited. For instance, the antiviral pleconaril may have a marginal treatment effect against HRV, which is however outweighed by the risk of its side effects. Accordingly, the United States Food and Drug Administration (FDA) rejected approval of pleconaril for treatment of the common cold (Fleischer and Laessig, 2003).

It is thus an object of the present invention to provide a prevention or treatment which is relatively safe and effective against an HRV infection, such as the common cold or a lower respiratory tract infection, especially in an immunosuppressed individual or in an individual having COPD or asthma.

SUMMARY OF THE INVENTION

Therefore, the present invention provides a pharmaceutical composition for use in prevention or treatment of an HRV infection. The composition comprises an aldohexose (in particular a D-aldohexose) such as glucose (preferably D-glucose) wherein the hydroxyl group at carbon 2 of the aldohexose is replaced by any one of the following substituents: H, F, Cl, Br, I, SH, methyl (Me), methoxy (OMe) and methylmercapto (SMe). Herein, an aldohexose compound according to this definition is also called "the modified aldohexose". In an especially preferred embodiment, the modified aldohexose is 2-deoxy-glucose.

In a further aspect, the present invention relates to a dispenser for intranasal administration such as a nasal spray, containing a pharmaceutical composition comprising an aldohexose wherein the hydroxyl group at carbon 2 of the aldohexose is replaced by any one of H, F, Cl, Br, I, SH, Me, OMe and SMe, in particular 2-deoxy-D-glucose.

In another aspect, the present invention relates to an inhalation device, such as a metered-dose inhaler, a dry-powder inhaler or a nebuliser, for administration of a pharmaceutical composition preferably to the lower respiratory tract, comprising a pharmaceutical composition comprising an aldohexose, wherein the hydroxyl group at carbon 2 of the aldohexose is replaced by any one of H, F, Cl, Br, I, SH, Me, OMe and SMe, preferably 2-deoxy-D-glucose.

In yet another aspect of the present invention, a method for delaying the onset of or treating an HRV infection, comprising obtaining a pharmaceutically acceptable formulation comprising an aldohexose, wherein the hydroxyl group at carbon 2 is replaced by any one of H, F, Cl, Br, I, SH, Me, OMe and SMe; and administering an effective amount of the formulation to an individual having the HRV infection or at risk of developing the HRV infection, is provided.

Figure 3:
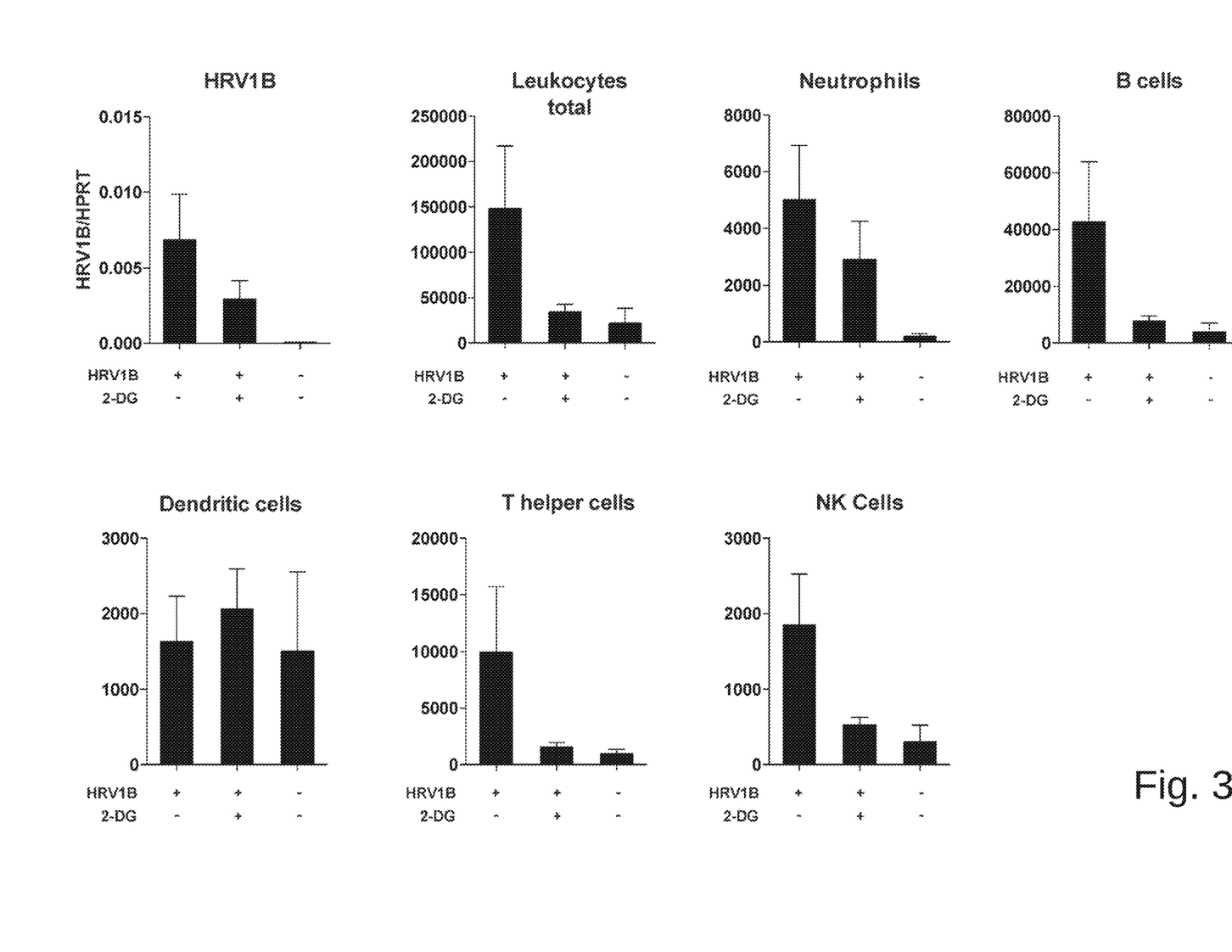
FIG. 3: 2-deoxyglucose reduces viral load and ameliorates inflammation caused by HRV airway infection in vivo. C57BL/6 mice were infected with HRV 1B intranasally ±50 µL 5 mM 2-DG/50 µL PBS. After 24 h of infection, mice were euthanized, a bronchioalveolar lavage (BAL) performed and tissue obtained for qPCR and histological analysis. Shown is the presence of HRV1B RNA in lung tissue normalized to hypoxanthine ribosyltransferase (HPRT) expression, indicative of viral load, and the count of leukocyte populations in the BAL (Total leukocytes=CD45+, Neutrophils=CD45+Ly6G+, B cells=CD45+CD19+, dendritic cells=CD45+CD11c+, T helper cells=CD45+CD3+ CD4+, NK cells=CD45+NK1.1+), indicative of lung inflammation.
Figure 4:
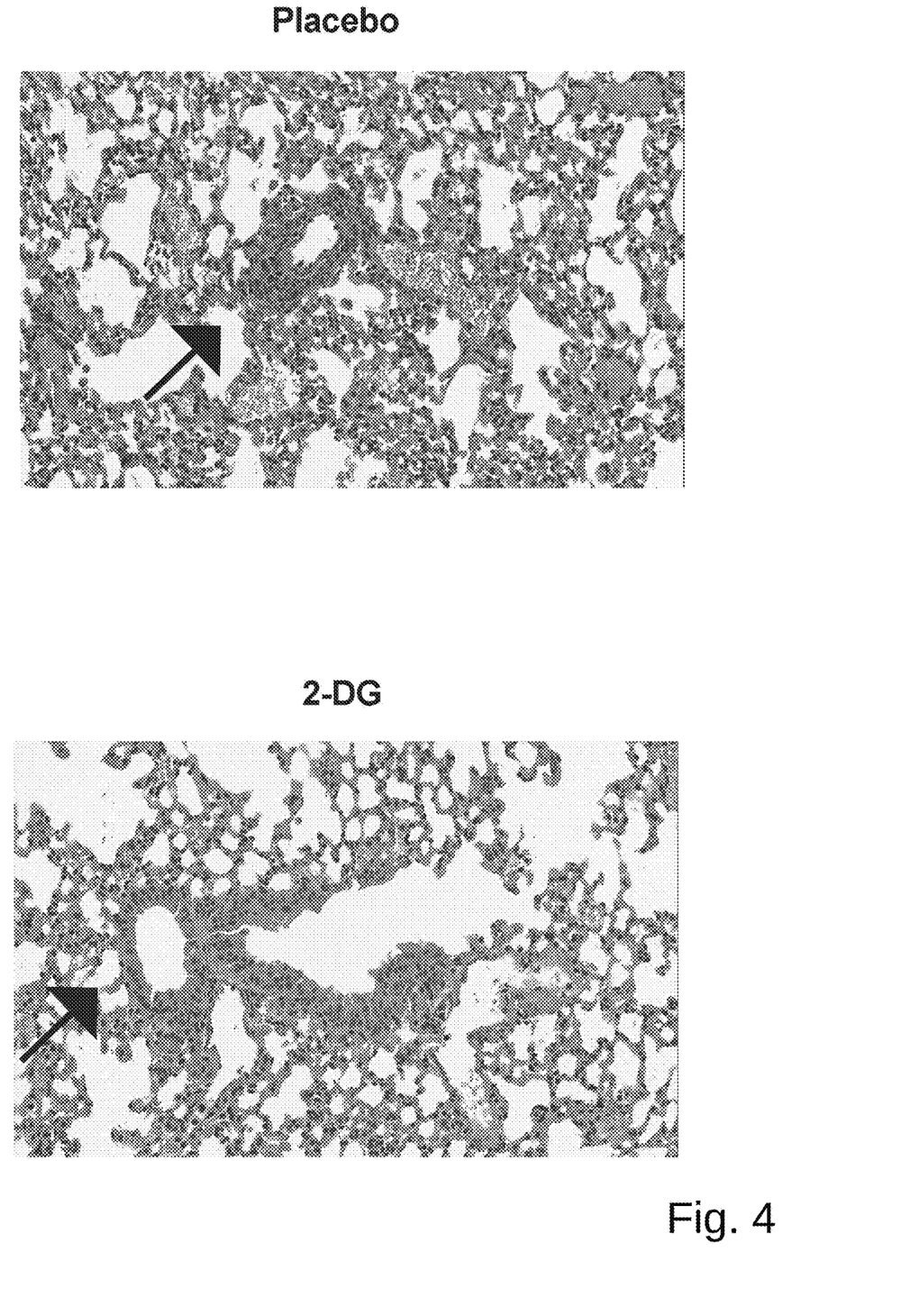
FIG. 4: 2-deoxyglucose ameliorates inflammation caused by HRV airway infection in vivo, as confirmed by histology. Depicted are two representative haematoxylin and eosin (HE) stains of lung tissues of HRV-challenged mice treated with placebo or 2-DG. A representative experiment of 2 independent experiments performed is shown. In each experiment, 10 mice per infection group were tested and 2 mice in the uninfected control-group. The placebo treated mouse has markedly more peribronchiolar leukocyte infiltration than the 2-DG treated mouse.

In the course of the present invention, it was surprisingly found that treatment with the modified aldohexose effectively inhibits HRV reproduction in-vitro (cf. example 1 and FIGS. 1 and 2) as well as in vivo (cf. example 2 and FIGS. 3 and 4), without any measurable impact on cell viability. In vivo, no side effects were observed in connection with the inventive treatment. As the modified aldohexose targets HRV replication itself, it is effective when administered after an HRV infection has occurred (e.g. when the individual has already fallen ill with the common cold) as well as when administered before an HRV infection has occurred (i.e. as a prophylactic measure, e.g. to delay or completely avoid onset of the disease or ameliorate or completely suppress the symptoms of the disease). For instance, prophylactic administration may be appropriate if a family member already shows symptoms of rhinitis.

While 2-deoxy-glucose was disclosed in the prior art to be effective against some enveloped viruses such as influenza virus (see e.g. Kilbourne, 1959 and Courtney et al., 1973), the prior art did not suggest at all that 2-deoxy-glucose is effective against HRV infection. Specifically, influenza virus and HRV are both very distinct in their structure and pathophysiology. Influenza virus belongs to the unrelated family of orthomyxoviridae, is enveloped and binds to sialic acid expressing receptors for infection of epithelial cells (see Sun and Whittaker, 2013). In contrast, HRV is non-enveloped and most subtypes bind to ICAM-1 for host cell entry (Blaas and Fuchs, 2016). Apart from these differences, the viruses evolved very different strategies in endosomal escape and translation initiation (see Blaas and Fuchs, 2016, and Watanabe and Kawaoka, 2015). Consequently, the state-of-the art therapy against influenza virus infections, oseltamivir, is not effective against HRV. Moreover, an inhibitory capacity of 2-deoxy-glucose on any human-pathogenic non-enveloped RNA viruses (such as HRV) was not known in the prior art (cf. e.g. Kang and Hwang, 2006), making the effectiveness of the inventive HRV treatment all the more surprising.

Completely unrelated to therapy, let alone prevention or treatment of a HRV infection, Ojima et al. (Annals of nuclear medicine 3 (1989): 143-147) describe the preparation of a fine powder of 2-deoxy-2-($^{18}$F)fluoro-D-glucose ($^{18}$FDG) suitable for inhalation to diagnose non-infectious lung diseases by means of positron emission tomography (PET). Also Venegas et al. (Database CA, Chemical Abstracts Service, Database accession no. 2013:196451) describe the use of $^{18}$FDG for PET imaging of the lung, again merely for diagnostic purposes and entirely unrelated to viral infection, let alone HRV infection.

Also unrelated to RNA viruses, DE 197 06 489 A1 discloses the use of 2-deoxy-glucose for the suppression of viral DNA transcription in virus-associated lesions and/or neoplasms, which are caused by DNA viruses (e.g. human papillomavirus, hepatitis B virus, Epstein-Barr virus).

Kang and Hwang describe the role of 2-deoxy-glucose as an anticancer and antiviral therapeutic. It is disclosed that 2-deoxy-glucose can inhibit multiplication of some enveloped viruses (influenza virus, sindbis virus and semliki forest virus, herpes simplex virus, respiratory syncytial virus and measles virus) by inhibiting viral envelope biosynthesis and virion assembly. No inhibitory capacity on any non-enveloped RNA viruses is disclosed.

The effects of 2-deoxy-glucose on enveloped viruses have been described in the prior art. For example, Schnitzer et al. (Virology 67 (1975) 306-309) describe the effect of 2-deoxy-glucose and glucosamine on the growth and functions of respiratory syncytial and parainfluenza 3 viruses. Kilbourne (Nature 183 (1959) 271-272) discloses the inhibition of influenza virus multiplication by 2-deoxy-glucose. Hodes et al. (Virology 63 (1975) 201-208) describe the inhibition of respiratory syncytial, parainfluenza 3 and measles viruses by 2-deoxy-glucose. However, prior to the present invention there was no indication that 2-deoxy-glucose could also be effective against non-enveloped RNA viruses.

Unrelated to 2-deoxy-glucose, Arita et al. (Carbohydrate Research 62 (1978) 143-154) disclose the synthesis of a variety of analogues and derivatives of phenyl glycosides and the examination of their antiviral activity against some enveloped viruses (influenza virus and Herpes simplex virus).

In connection with all aspects of the present invention, the modified aldohexose contained in the pharmaceutical composition (or pharmaceutically acceptable formulation) preferably is one of compounds I-VIII (depicted as Fischer projections):

wherein R is any one of H, F, Cl, Br, I, SH, Me, OMe and SMe. In other words, R replaces the hydroxyl group at carbon 2 of the respective aldohexose. Compound I (i.e. the compound based on D-glucose) is particularly preferred. 2-deoxy-D-glucose is compound I wherein R is H. 2-deoxy-D-glucose is also called "2-DG" herein.

At present, three HRV species are known, namely Rhinovirus A, B and C. An overview over HRV taxonomy is for instance given in Palmenberg et al., 2009. Preferably, in connection with all aspects of the present invention, the HRV to be treated or prevented is a Rhinovirus A or B.

In the context of the present invention, the expression "pharmaceutical composition" refers to any composition comprising at least one active agent (e.g. the modified aldohexose), and preferably one or more excipients, which is pharmaceutically acceptable for administration (in particular for topical administration or intranasal administration) to an individual, especially a mammal, in particular a human. Suitable excipients are known to the person skilled in the art, for example water (especially water for injection), saline, Ringer's solution, dextrose solution, buffers, Hank solution, vesicle forming compounds (e.g. lipids), fixed oils, ethyl oleate, 5% dextrose in saline, substances that enhance isotonicity and chemical stability, buffers and preservatives, such as benzalkonium chloride. The pharmaceutical composition according to the present invention may be liquid or ready to be dissolved in liquid such as sterile, deionised or distilled water, or sterile isotonic phosphate-buffered saline (PBS). Preferably, 1000 µg (dry-weight) of such a composition comprises or consists of 0.1-990 µg, preferably 1-900 µg, more preferably 10-200 µg modified aldohexose, and optionally 1-500 µg, preferably 1-100 µg, more preferably 5-15 µg (buffer) salts (preferably to yield an isotonic buffer in the final volume), and optionally 0.1-999.9 µg, preferably 100-999.9 µg, more preferably 200-999 µg other excipients. Preferably, 100 mg of such a dry composition is dissolved in sterile, de-ionised/distilled water or sterile isotonic phosphate-buffered saline (PBS) to yield a final volume of 0.1-100 ml, preferably 0.5-20 ml, more preferably 1-10 ml. The dosage and method of administration, however, typically depends on the individual to be treated. In general, the modified aldohexose may be administered at a dose of between 1 µg/kg and 10 mg/kg, more preferably between 10 µg/kg and 5 mg/kg, most preferably between 0.1 and 2 mg/kg.

According to a particularly preferred embodiment of the present invention, the pharmaceutical composition is liquid and preferably an aqueous solution. In general, liquid compositions are especially suitable for intranasal administration, which is the preferred mode of administration.

In a further preferment, the concentration of the modified aldohexose, in particular 2-deoxy-D-glucose, is 0.01 mM-1000 mM, preferably 0.1 mM-500 mM, more preferably 0.25 mM-250 mM, even more preferably 0.5 mM-100 mM, in particular 1 mM-50 mM or even 2.5 mM-25 mM. These concentration ranges are relatively safe and effective in connection with the inventive treatment.

The pharmaceutical composition may comprise further active agents, in particular to further increase effectiveness or achieve further symptom reduction of the common cold. Thus, according to a further preferred embodiment, the pharmaceutical composition further comprises at least one additional active agent. Preferably, the additional active agent is selected from the group consisting of decongestants, in particular norepinephrine releasing agents (such as pseudoephedrine, ephedrine and phenylpropanolamine), α-adrenergic receptor agonists (such as oxymetazoline and xylometazoline), and corticosteroids (such as budesonide, flunisolide, and fluticasone), and nonsteroidal anti-inflammatory drugs (NSAIDs) such as acetylsalicylic acid, ibuprofen, diclofenac, and phenylbutazone. Such agents can be expected to act synergistically together with the modified aldohexose against a rhinovirus infection such as rhinitis or the common cold. By contrast, the modified aldohexose such as 2-deoxy-D-glucose may also be the single active agent in the pharmaceutical composition (preferably in the presence of one or more excipients).

The individual to be treated according to the present invention is preferably a human individual, in particular an immunosuppressed individual or an individual having COPD or asthma. According to a preferred embodiment, a dose of the pharmaceutical composition is administered to a human individual, preferably intranasally (in other words: into a nostril of the individual, preferably into each nostril independently) and/or to a mucosal membrane, preferably a mucosal membrane of the respiratory tract, in particular a mucosal membrane of the nasal cavity or of the lower respiratory tract. Advantageously, the dose is administered at least once every other day, preferably at least once per day, more preferably at least twice per day, in particular at least thrice per day, and preferably for 2-14 days, more preferably for 3-10 days, in particular for 4-7 days.

For relatively safe and effective treatment, according to a preference, the total amount of the modified aldohexose, in particular 2-deoxy-D-glucose, in the dose is 0.001 µmol-100 mol, preferably 0.01 µmol-50 mol, more preferably 0.025 µmol-25 mol, even more preferably 0.05 µmol-5 mol, in particular 0.1 µmol-2.5 µmol or even 0.2 µmol-1.25 mol.

According to a particularly preferred embodiment, the pharmaceutical composition (or pharmaceutically acceptable formulation) according to the present invention is used for prevention or treatment of the common cold, a rhinitis or a lower respiratory tract infection, especially in an immunosuppressed individual or in an individual having COPD or asthma. The term "preventing" or "prevention" as used herein means to stop a disease state or condition from occurring in an individual completely or almost completely or at least to a (preferably significant) extent, especially when the individual is predisposed to such a risk of contracting a disease state or condition.

The dispenser for intranasal administration of the pharmaceutical composition described hereinabove is preferably a nasal spray or a nose drop applicator. Nasal sprays and nose drop applicators are known in the art and e.g. disclosed in U.S. Pat. Nos. 2,577,321, 6,000,580 or EP 0 170 198 A2. As used herein, the term "nose drop applicator" refers to any dispenser suitable for, especially intended for, the administration of nose drops.

The inhalation device for administration of the pharmaceutical composition described hereinabove (preferably to the lower respiratory tract) is preferably a metered-dose inhaler, a dry-powder inhaler or a nebuliser.

A metered-dose inhaler is a device that aerosolises a pre-defined dose of a pharmaceutical composition (i.e. produces a comparatively short burst of aerosol with a defined dose), usually for self-administration by the patient. A metered-dose inhaler is for instance disclosed in U.S. Pat. No. 6,260,549 B1.

Dry-powder inhalers are devices for inhalation of dry-powder formulations by the patient. Such devices are for instance disclosed in U.S. Pat. Nos. 4,995,385 and 4,069,819. Established dry-powder inhalers are for instance SPIN-HALER®, ROTAHALER®, FLOWCAPS®, INHALATOR®, DISKHALER® and AEROLIZER®.

Nebulisers are devices that produce aerosols for inhalation, typically continuously as long as they are switched on or breath-actuated. Established nebuliser products are for instance Aeroneb® and Pari®. Document U.S. Pat. No. 9,364,618 B2, e.g., also discloses a nebuliser.

BRIEF DESCRIPTION OF THE DRAWINGS

The present invention is further illustrated by the following figures and examples, without being restricted thereto.

FIG. 1: 2-deoxyglucose inhibits HRV replication and HRV protein expression in vitro. Panel A) shows the impact of 2-DG on HRV 14 replication in HeLa Ohio cells and primary human fibroblasts. Cells were infected for 1 h and washed in PBS before application of the agent in the indicated concentration and incubation in full growth medium for additional 6 h. After the incubation period, RNA was obtained and reversely transcribed to cDNA before assessing viral RNA load by qPCR. A summary of 6 independent experiments is shown. *p<0.05 calculated by Wilcoxon signed rank test of the normalized data. Panel B) shows the expression of viral proteins VP1-3 in HRV 14 infected HeLa Ohio cells. Cells were infected as above ±2-DG treatment prior to lysis and western blot analysis. A representative experiment of 2 independent experiments performed in duplicates is shown.

EXAMPLE 1—CELL CULTURE AND IN-VITRO HRV INFECTION

Experiments involving human material were carried out according to the Declaration of Helsinki principles after approval by the ethics committee of the Medical University of Vienna and after obtaining written informed consent from the participants (vote number 1149/2011: isolation and culture of cells from and analysis of normal human skin biopsies).

HeLa cells (strain: Ohio, Flow laboratories) were cultivated in RPMI 1640 supplemented with 2 mM 1-glutamine, (both Gibco Ltd., Paisley, Scotland), 100 U/mL penicillin, 100 µg/mL streptomycin (PAA Laboratories, Austria) and 10% FCS (Gibco). For fibroblast isolation, tissue samples including skin and subcutaneous fat (100-300 $cm^2$) were obtained from patients undergoing routinely performed body contouring surgeries and were used for the isolation of mast cells, fibroblasts, and keratinocytes. The skin was inconspicuous upon clinical inspection and in histology. Subcutaneous tissue and reticular dermis were removed and the remaining split thickness skin was cut into 0.5 $cm^2$ pieces and placed overnight at 4° C. in 2.4 U/ml dispase II (Roche, Vienna, Austria). After the separation of the epidermis, dermis was digested in collagenase I (Gibco, Vienna, Austria) at 37° C. for 2 h. CD117+ mast cells were isolated using magnetic beads (MACS System; Miltenyi Biotec, Bergisch Gladbach, Germany) according to the manufacturer's instructions. To increase the purity of recovered cells, magnetic isolation was repeated with CD117+ cells from the first isolation round. CD117+ mast cells were then seeded in DMEM (Gibco) supplemented with 10% FCS, penicillin/streptomycin (both Biochrom, Berlin, Germany), and 100 ng/ml recombinant human stem cell factor (PeproTech, Rocky Hill, N.Y., USA). After the isolation of mast cells, CD117 adherent cells (=fibroblasts) were cultured in supplemented RPMI 1640 as above. (Gschwandtner et al., 2017)

HeLa Ohio cells or fibroblasts were plated on polystyrene plates overnight (Corning Incorporated, Corning, N.Y., USA). On the subsequent day, cells were infected with the indicated amount of 50% Tissue culture Infective Dose (TCID 50) of HRV 14 (belonging to species Rhinovirus B) per cell (multiplicity of infection 3.5-10, depending on the experiment). After 1 h of infection, cells were washed with 37° C. phosphate-buffered saline (PBS) and incubated another 6 h with medium±the indicated agent in the indicated concentration before further processing. For assessment of cell viability, cells were stained with a fixable viability dye (65-0865-14; eBioscience, Vienna, Austria).

Western blot analysis: HeLa Ohio cells were infected as described above. After 7 h of infection, cells were lysed in 0.5% Triton-X buffer for 5 min on ice. After lysis, the suspension was centrifuged for 5 min at 13000×g, and the supernatant was utilized for further analysis. Western blot analysis was performed as described before (Gualdoni et al., 2015). Anti-HRV VP1-3 antibody and anti-GAPDH were used in a dilution of 1:1000. Detection was performed with Pierce® ECL Western blotting substrate (Thermo Fisher Scientific, Waltham, Mass.) on a LAS-4000 (Fujifilm, Tokyo, Japan). Data analysis, quantification, and processing were performed with Fiji (ImageJ) image processing software.

Figure 1:
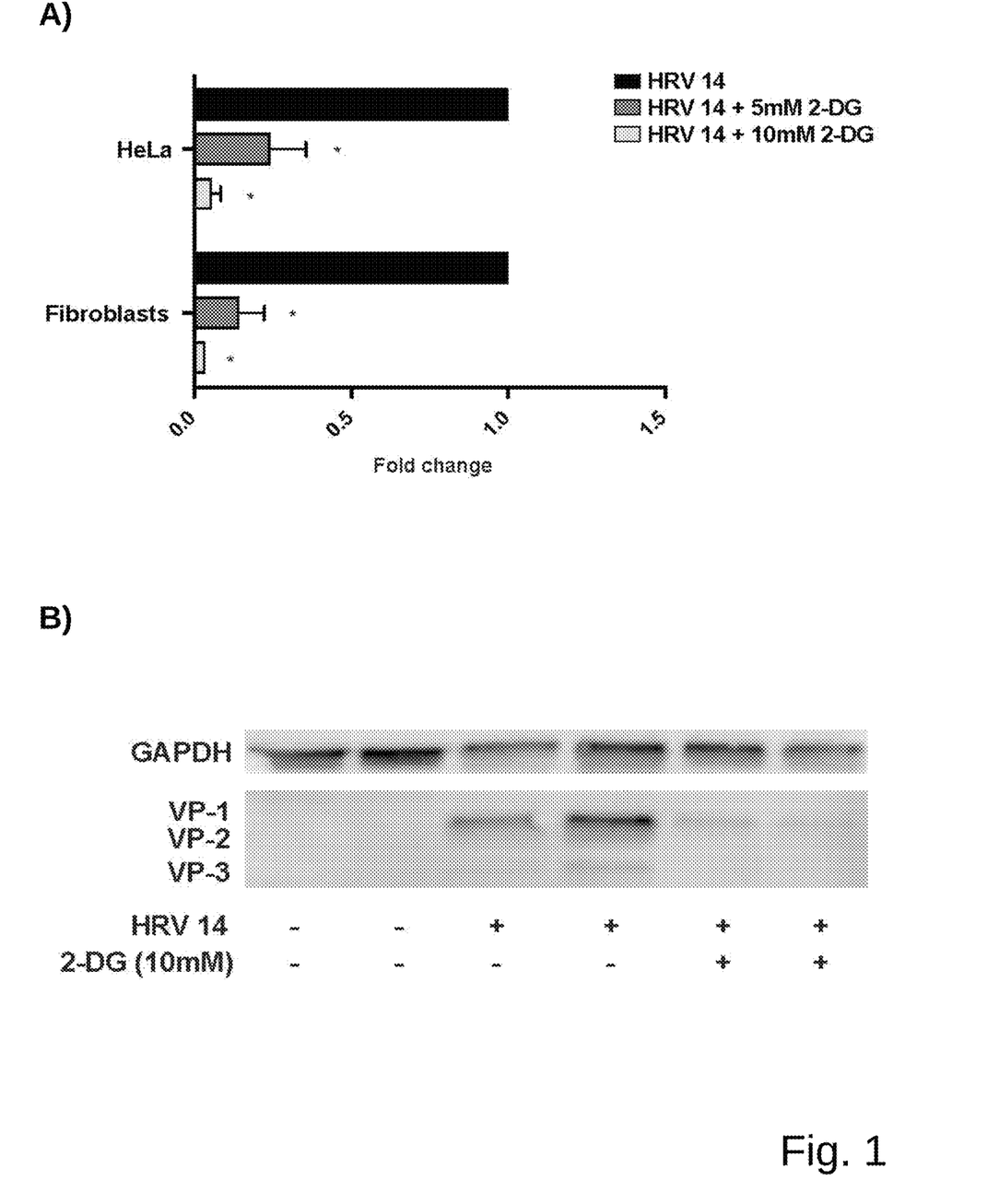
Figure 2:
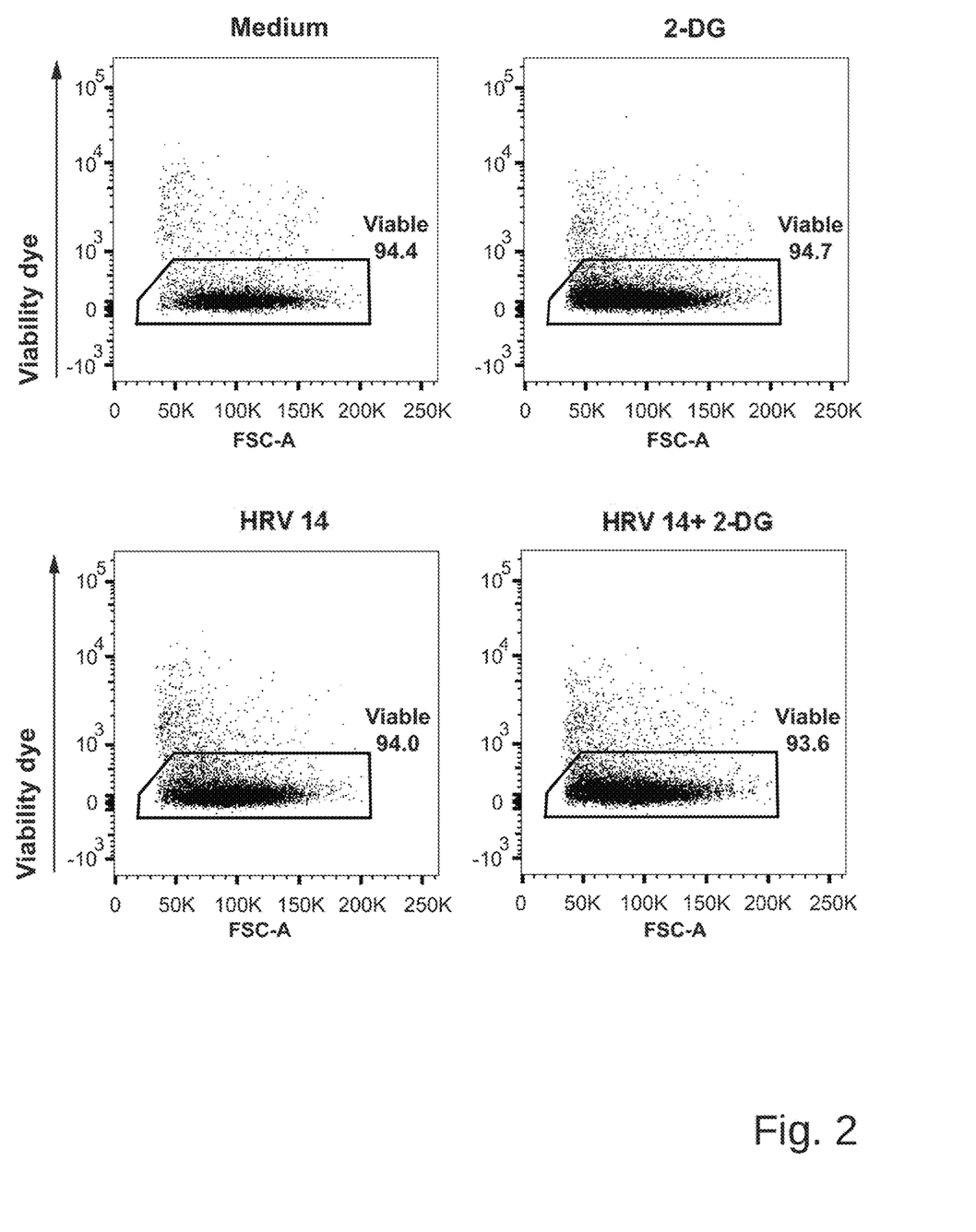
FIG. 2: 2-deoxyglucose is not toxic to human cells. Treatment with 10 mM 2-deoxyglucose (in the presence or absence of HRV) has no significant influence on cell viability of HeLa cells. Cells were infected and treated as above before application of a fluorescently labeled viability dye and flow cytometric assessment.

Results:

2-deoxyglucose strongly inhibited HRV reproduction both in HeLa cells and in primary human fibroblasts (see FIG. 1A). To verify this impact on reproduction, the viral replication on protein level as mirrored by the expression of viral protein (VP) 1-3 in HeLa cells was also analysed, which showed similar results as on RNA level (FIG. 1A). The agent 2-deoxyglucose had no measurable impact on cell viability in the utilized doses (FIG. 2).

EXAMPLE 2—MURINE HRV INFECTION MODEL

All animal experimentation protocols were evaluated by the Animal Ethics Committee of the Medical University of Vienna and approved by the Ministry of Economy and Science (BMWFW-66.009/0356_WF/V/3b/2015). Animal husbandry and experimentation was performed according to the Federation of Laboratory Animal Science Association guidelines. Female C57BL/6 J mice aged 6 to 8 wk from in-house breeding (originally obtained from The Jackson Laboratory, Bar Harbor, Me., USA) were used for all experiments. An animal care professional not related to the study performed allocation of mice to the groups randomly.

Experiments were performed according to a published protocol (Bartlett et al., 2008) with minor modifications. Mice were sedated with isoflurane and an inoculum of $5\times10^6$ TCID50 of HRV1B (belonging to species Rhinovirus A) in PBS was applied intranasally. Either 5 mM 2-DG dissolved in PBS or PBS solo were simultaneously applied intranasally. After 24 h, mice were euthanized and a bronchioalveolar lavage performed. One lung lobe was obtained for PCR analysis and one for histological examination. For PCR analysis, material was homogenized before RNA isolation with the RNEasy kit as above. For histological analysis, lung lobes were fixed in 10% formaldehyde and embedded in paraffin. Lung sections (4 µm) were stained with H&E and evaluated by a pathologist blinded to group allocation.

Results:

In this well-established murine model of rhinovirus airway infection (Bartlett et al., 2008), 2-DG reduced HRV load in infected lung tissue and reduced virus induced lung inflammation (see FIGS. 3 and 4), in line with the in vitro findings. There were no observable side effects on the treated mice at all.

EXAMPLE 3—NASAL SPRAY

A nasal spray as e.g. disclosed in U.S. Pat. No. 6,000,580 is provided containing 10 ml of the following pharmaceutical composition: 10 mM 2-deoxy-D-glucose, 0.9% w/v NaCl dissolved in sterile deionised water.

EXAMPLE 4—NOSE DROP APPLICATOR

A nose drop applicator as e.g. disclosed in EP 0 170 198 A2 is provided containing 5 ml of the following pharmaceutical composition: 0.5 mM 2-deoxy-2-fluoro-D-mannose, 0.05% (w/v) oxymetazoline hydrochloride, 0.05% (w/w) benzalkonium chloride, 85% (v/v) glycerol in sterile deionised water.

EXAMPLE 5—NEBULIZER

A nebuliser as e.g. disclosed in U.S. Pat. No. 9,364,618 B2 is provided comprising the following pharmaceutical composition in its fluid reservoir: 35 mM 2-deoxy-D-glucose, 0.9% w/v NaCl dissolved in sterile deionised water. The nebuliser is used to deliver the composition by inhalation as an aerosol to the lower respiratory tract of an immune-suppressed patient suffering from a rhinovirus infection in the lungs.

NON-PATENT REFERENCES

Bartlett, N. W., Walton, R. P., Edwards, M. R., Aniscenko, J., Caramori, G., Zhu, J., Glanville, N., Choy, K. J., Jourdan, P., Burnet, J., et al. (2008). Mouse models of rhinovirus-induced disease and exacerbation of allergic airway inflammation. Nat. Med. 14, 199-204.

Bertino, J. S. (2002). Cost burden of viral respiratory infections: issues for formulary decision makers. Am. J. Med. 112 Suppl 6A, 42S-49S.

Blaas, D. and Fuchs, R. (2016) Mechanism of human rhinovirus infections. Mol. Cell. Pediatr. 3, 21.

Courtney, Richard J., Sheldon M. Steiner, and Matilda Benyesh-Melnick. "Effects of 2-deoxy-D-glucose on herpes simplex virus replication." Virology 52.2 (1973): 447-455.

Fleischer and Laessig. "Safety and efficacy evaluation of pleconaril for treatment of the common cold." Clinical infectious diseases 37.12 (2003): 1722-1722.

Gschwandtner, M., Paulitschke, V., Mildner, M., Brunner, P. M., Hacker, S., Eisenwort, G., Sperr, W. R., Valent, P., Gerner, C., and Tschachler, E. (2017). Proteome analysis identifies L1CAM/CD171 and DPP4/CD26 as novel markers of human skin mast cells. *Allergy* 72, 85-97.

Gualdoni, G. A., Lingscheid, T., Schmetterer, K. G., Hennig, A., Steinberger, P., and Zlabinger, G. J. (2015). Azithromycin inhibits IL-1 secretion and non-canonical inflammasome activation. Sci. Rep. 5, 12016.

Kaiser, L., Aubert, J.-D., Pache, J.-C., Deffernez, C., Rochat, T., Garbino, J., Wunderli, W., Meylan, P., Yerly, S., Perrin, L., et al. (2006). Chronic rhinoviral infection in lung transplant recipients. Am. J. Respir. Crit. Care Med. 174, 1392-1399.

Kang, Hyun Tae, and Eun Seong Hwang. "2-Deoxyglucose: an anticancer and antiviral therapeutic, but not any more a low glucose mimetic." Life sciences 78.12 (2006): 1392-1399.

Kilbourne, Edwin D. "Inhibition of influenza virus multiplication with a glucose antimetabolite (2-deoxy-D-glucose)." Nature 183.4656 (1959): 271-272.

Liu, M., Mallory, G. B., Schecter, M. G., Worley, S., Arrigain, S., Robertson, J., Elidemir, O., and Danziger-Isakov, L. A. (2010). Long-term impact of respiratory viral infection after pediatric lung transplantation. Pediatr. Transplant. 14, 431-436.

Palmenberg, Ann C., et al. "Sequencing and analyses of all known human rhinovirus genomes reveal structure and evolution." Science 324.5923 (2009): 55-59.

Papi, A., Bellettato, C. M., Braccioni, F., Romagnoli, M., Casolari, P., Caramori, G., Fabbri, L. M., and Johnston, S. L. (2006). Infections and airway inflammation in chronic obstructive pulmonary disease severe exacerbations. Am. J. Respir. Crit. Care Med. 173, 1114-1121.

Steinke, J. W., and Borish, L. (2016). Immune Responses in Rhinovirus-Induced Asthma Exacerbations. Curr. Allergy Asthma Rep. 16.

Sun, X. and Whittaker, G. R. (2013) Entry of influenza virus. Adv. Exp. Med. Biol. 790, 72-82.

Watanabe, T. and Kawaoka, Y. (2015) Influenza virus-host interactomes as a basis for antiviral drug development. Curr. Opin. Virol. 14, 71-78.

The invention claimed is:

1. A method for delaying the onset of or treating an HRV infection, comprising:
    obtaining a pharmaceutically acceptable formulation comprising 2 deoxy-D-glucose; and
    administering an effective amount of the formulation to an individual having the HRV infection or at risk of developing the HRV infection.

2. The method of claim 1, wherein the formulation is a liquid aqueous solution.

3. The method of claim 1, wherein the concentration of 2-deoxy-D-glucose in the formulation is 0.1 mM -500 mM.

4. The method of claim 1, wherein the concentration of 2-deoxy-D-glucose in the formulation is 0.25 mM-250 mM.

5. The method of claim 1, wherein the formulation comprises at least one excipient or at least one additional active agent.

6. The method of claim 1, wherein the 2-deoxy-D-glucose is administered at a dose of 0.01 µmol-50 µmol.

7. The method of claim 6, wherein the formulation is administered at least twice per day for 2-14 days.

8. The method of claim 1, wherein the formulation is administered to a mucosal membrane of the respiratory tract.

9. The method of claim 1, wherein the individual has or is at risk of developing a common cold, a rhinitis, or a lower respiratory tract infection.

10. The method of claim 1, wherein the individual is immunosuppressed.

11. The method of claim 1, wherein the individual has COPD or asthma.

12. The method of claim 1, wherein the formulation is administered into a nostril of the individual.

* * * * *

UNITED STATES PATENT AND TRADEMARK OFFICE
CERTIFICATE OF CORRECTION

| | |
|---|---|
| PATENT NO. | : 11,413,298 B2 |
| APPLICATION NO. | : 16/770482 |
| DATED | : August 16, 2022 |
| INVENTOR(S) | : Johannes Stockl and Guido Gualdoni |

It is certified that error appears in the above-identified patent and that said Letters Patent is hereby corrected as shown below:

On the Title Page

Item (54) and in the Specification, Column 1, Line 1, Delete "MEDICAMENT FOR PREVENTION OF TREATMENT OF RHINOVIRUS INFECTION" and replace with -- MEDICAMENT FOR PREVENTION OR TREATMENT OF RHINOVIRUS INFECTION --.

Signed and Sealed this
Twenty-fifth Day of October, 2022

Katherine Kelly Vidal
*Director of the United States Patent and Trademark Office*